(12) United States Patent
Inamdar

(10) Patent No.: US 10,299,803 B2
(45) Date of Patent: May 28, 2019

(54) SELF-ALIGNING DRIVE COUPLER

(71) Applicant: COVIDIEN LP, Mansfield, MA (US)

(72) Inventor: Tejas Inamdar, Boston, MA (US)

(73) Assignee: COVIDIEN LP, Mansfield, MA (US)

( * ) Notice: Subject to any disclaimer, the term of this patent is extended or adjusted under 35 U.S.C. 154(b) by 257 days.

(21) Appl. No.: 15/228,628

(22) Filed: Aug. 4, 2016

(65) Prior Publication Data

US 2018/0036026 A1    Feb. 8, 2018

(51) Int. Cl.
| | | |
|---|---|---|
| *F16D 1/10* | (2006.01) | |
| *A61B 17/00* | (2006.01) | |
| *A61B 17/16* | (2006.01) | |
| *A61B 17/32* | (2006.01) | |
| *A61B 17/3207* | (2006.01) | |
| *A61B 17/3205* | (2006.01) | |

(52) U.S. Cl.
CPC ...... *A61B 17/162* (2013.01); *A61B 17/32002* (2013.01); *F16D 1/101* (2013.01); *A61B 17/320758* (2013.01); *A61B 2017/0046* (2013.01); *A61B 2017/00477* (2013.01); *F16D 2001/102* (2013.01)

(58) Field of Classification Search
CPC .. A61B 2017/00477; A61B 2017/0046; A61B 2017/00398; A61B 2017/00526; A61B 2017/00734; A61B 17/32002; A61B 17/320758; A61B 2017/320775; A61B 17/320016; A61B 2017/320024; A61B 2017/00486; A61B 17/3205; F16D 1/10; F16D 2001/102; F16D 2001/103; F16D 1/04; F16D 1/0817
See application file for complete search history.

(56) References Cited

U.S. PATENT DOCUMENTS

| | | | |
|---|---|---|---|
| 1,585,934 A | 5/1926 | Muir | |
| 1,666,332 A | 4/1928 | Hirsch | |
| 1,831,786 A | 11/1931 | Duncan | |
| 2,708,437 A | 5/1955 | Hutchins | |
| (Continued) | | | |

FOREIGN PATENT DOCUMENTS

| | | | |
|---|---|---|---|
| DE | 3206381 A1 | 9/1983 | |
| DE | 3339322 A1 | 5/1984 | |
| (Continued) | | | |

OTHER PUBLICATIONS

Notification of Transmittal of the International Search Report and the Written Opinion of the International Searching Authority, or the Declaration issued in corresponding application No. PCT/US2016/045556 dated Apr. 10, 2017.

*Primary Examiner* — Katrina M Stransky

(57) ABSTRACT

Systems and methods herein are associated with a handpiece, a drive hub, a drive coupler, and an instrument comprising an elongate shaft and resection member telescoped within the elongate shaft, the resection member coupled to the drive hub. The drive hub comprises an interior surface and an exterior surface, the interior surface defines a cross-sectional shape, and the drive hub is coupled to a drive shaft of a motor of the handpiece. The drive coupler comprises a first lobe extending radially from a central axis of the drive coupler, the drive coupler is telescoped at least partially within the drive hub such that the first lobe that engages with a portion of the cross-sectional shape.

26 Claims, 7 Drawing Sheets

(56) References Cited

U.S. PATENT DOCUMENTS

| | | |
|---|---|---|
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,073,160 A | 2/1978 | Perret |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,411,513 A | 5/1995 | Ireland et al. |
| 5,425,376 A | 6/1995 | Banys et al. |
| 5,429,601 A | 7/1995 | Conley et al. |
| 5,443,476 A | 8/1995 | Shapiro |
| 5,449,356 A | 9/1995 | Walbrink et al. |
| 5,456,689 A | 10/1995 | Kresch et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |

(56) References Cited

U.S. PATENT DOCUMENTS

| | | | |
|---|---|---|---|
| 6,004,320 | A | 12/1999 | Casscells et al. |
| 6,007,513 | A | 12/1999 | Anis et al. |
| 6,024,751 | A | 2/2000 | Lovato et al. |
| 6,032,673 | A | 3/2000 | Savage et al. |
| 6,039,748 | A | 3/2000 | Savage et al. |
| 6,042,552 | A | 3/2000 | Cornier |
| 6,068,641 | A | 5/2000 | Varsseveld |
| 6,086,542 | A | 7/2000 | Glowa et al. |
| 6,090,123 | A | 7/2000 | Culp et al. |
| 6,113,594 | A | 9/2000 | Savage |
| 6,119,973 | A | 9/2000 | Galloway |
| 6,120,147 | A | 9/2000 | Vijfvinkel et al. |
| 6,120,462 | A | 9/2000 | Hibner et al. |
| 6,132,448 | A | 10/2000 | Perez et al. |
| 6,149,633 | A | 11/2000 | Maaskamp |
| 6,156,049 | A | 12/2000 | Lovato et al. |
| 6,159,160 | A | 12/2000 | Hsei et al. |
| 6,159,209 | A | 12/2000 | Hakky |
| 6,203,518 | B1 | 3/2001 | Anis et al. |
| 6,217,543 | B1 | 4/2001 | Anis et al. |
| 6,224,603 | B1 | 5/2001 | Marino |
| 6,244,228 | B1 | 6/2001 | Kuhn et al. |
| 6,258,111 | B1 | 7/2001 | Ross et al. |
| 6,277,096 | B1 | 8/2001 | Cortella et al. |
| 6,315,714 | B1 | 11/2001 | Akiba |
| 6,358,200 | B1 | 3/2002 | Grossi |
| 6,358,263 | B2 | 3/2002 | Mark et al. |
| 6,359,200 | B1 | 3/2002 | Day |
| 6,402,701 | B1 | 6/2002 | Kaplan et al. |
| 6,428,486 | B2 | 8/2002 | Ritchart et al. |
| 6,494,892 | B1 | 12/2002 | Ireland et al. |
| 6,585,708 | B1 | 7/2003 | Maaskamp |
| 6,610,066 | B2 | 8/2003 | Dinger et al. |
| 6,626,827 | B1 | 9/2003 | Felix et al. |
| 6,632,182 | B1 | 10/2003 | Treat |
| 6,656,132 | B1 | 12/2003 | Omni |
| 6,712,773 | B1 | 3/2004 | Viola |
| 6,837,847 | B2 | 1/2005 | Ewers et al. |
| 7,025,732 | B2 | 4/2006 | Thompson et al. |
| 7,150,713 | B2 | 12/2006 | Shener et al. |
| 7,226,459 | B2 | 6/2007 | Cesarini et al. |
| 7,249,602 | B1 | 7/2007 | Emanuel |
| 7,510,563 | B2 | 3/2009 | Cesarini et al. |
| 7,763,033 | B2 | 7/2010 | Gruber et al. |
| 7,922,737 | B1 | 4/2011 | Cesarini et al. |
| 8,061,359 | B2 | 11/2011 | Emanuel |
| 9,060,801 | B1 | 6/2015 | Cesarini et al. |
| 2001/0039963 | A1 | 11/2001 | Spear et al. |
| 2001/0047183 | A1 | 11/2001 | Privitera et al. |
| 2002/0058859 | A1 | 5/2002 | Brommersma |
| 2003/0050603 | A1 | 3/2003 | Todd |
| 2003/0050638 | A1 | 3/2003 | Yachia et al. |
| 2003/0078609 | A1 | 4/2003 | Finlay et al. |
| 2003/0114875 | A1 | 6/2003 | Sjostrom |
| 2004/0204671 | A1 | 10/2004 | Stubbs et al. |
| 2005/0043690 | A1 | 2/2005 | Todd |
| 2005/0085692 | A1 | 4/2005 | Kiehn et al. |
| 2006/0025792 | A1* | 2/2006 | Gibson ............ A61B 17/2909 606/170 |
| 2006/0025793 | A1* | 2/2006 | Gibson ............ A61B 17/2909 606/170 |
| 2006/0036132 | A1 | 2/2006 | Renner et al. |
| 2006/0047185 | A1 | 3/2006 | Shener et al. |
| 2006/0241586 | A1 | 10/2006 | Wilk |
| 2008/0015621 | A1 | 1/2008 | Emanuel |
| 2008/0058588 | A1 | 3/2008 | Emanuel |
| 2008/0058842 | A1 | 3/2008 | Emanuel |
| 2008/0097468 | A1 | 4/2008 | Adams et al. |
| 2008/0097469 | A1 | 4/2008 | Gruber et al. |
| 2008/0097470 | A1 | 4/2008 | Gruber et al. |
| 2008/0097471 | A1 | 4/2008 | Adams et al. |
| 2008/0135053 | A1 | 6/2008 | Gruber et al. |
| 2008/0146872 | A1 | 6/2008 | Gruber et al. |
| 2008/0146873 | A1 | 6/2008 | Adams et al. |
| 2008/0245371 | A1 | 10/2008 | Gruber |
| 2008/0249366 | A1 | 10/2008 | Gruber et al. |
| 2008/0249534 | A1 | 10/2008 | Gruber et al. |
| 2008/0249553 | A1 | 10/2008 | Gruber et al. |
| 2008/0262308 | A1 | 10/2008 | Prestezog et al. |
| 2009/0270812 | A1 | 10/2009 | Litscher et al. |
| 2009/0270895 | A1 | 10/2009 | Churchill et al. |
| 2009/0270896 | A1 | 10/2009 | Sullivan et al. |
| 2009/0270897 | A1 | 10/2009 | Adams et al. |
| 2009/0270898 | A1 | 10/2009 | Chin et al. |
| 2010/0087798 | A1 | 4/2010 | Adams et al. |
| 2010/0152647 | A1 | 6/2010 | Shener et al. |
| 2014/0012236 | A1* | 1/2014 | Williams ......... A61B 17/07207 606/1 |
| 2015/0327905 | A1 | 11/2015 | Barth et al. |
| 2016/0278802 | A1* | 9/2016 | Cihak ............ A61B 17/32002 |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1623677 A1 | 2/2006 |
| EP | 1681022 A1 | 7/2006 |
| EP | 1820987 A2 | 8/2007 |
| GB | 2093353 A | 9/1982 |
| GB | 2311468 A | 10/1997 |
| JP | H0175416 U | 5/1989 |
| JP | 2002529185 A | 9/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 0012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 200195810 A2 | 12/2001 |
| WO | 02069808 A2 | 9/2002 |
| WO | 03022164 A1 | 3/2003 |

(56) References Cited

FOREIGN PATENT DOCUMENTS

| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 20070014548 A2 | 2/2007 |
| WO | 2007044833 A2 | 4/2007 |
| WO | 2012044705 A1 | 4/2012 |

* cited by examiner

SELF-ALIGNING DRIVE COUPLER

CROSS-REFERENCE TO RELATED APPLICATIONS

Not Applicable.

BACKGROUND

Surgical instrumentation may use handpieces to drive an instrument, and may employ a driver such as an electric motor. Rotational motion from the driver is transferred using a coupler, and the instrument may be engaged with the handpiece by pushing the instrument into the drive coupler and inserting the drive hub into the drive coupler, but the assembly may not be completed correctly because of a misalignment between the drive hub and drive coupler.

SUMMARY

In an embodiment, a surgical system comprising: a handpiece comprising a proximal end, a distal end, and a motor that defines a drive shaft; a drive hub comprising an interior surface, and an exterior surface, the interior surface defines a cross-sectional shape, and the drive hub coupled to the drive shaft; a drive coupler comprising a first lobe extending radially from a central axis of the drive coupler, the drive coupler telescoped at least partially within the drive hub such that the first lobe engages with a portion of the cross-sectional shape; and an instrument comprising an elongate shaft and resection member telescoped within the elongate shaft, the resection member coupled to the drive hub.

In an embodiment, a method of assembling a surgical device, comprising: telescoping a drive hub over a portion of a drive coupler along a central axis, the drive coupler comprising a first lobe extending radially outward; and thereby causing relative axial rotation as between the drive hub and the drive coupler until the first lobe of the drive coupler is aligned with and engages with a mating mechanism of the drive hub.

In an alternate embodiment, a handpiece for a surgical system, the handpiece comprising: an outer cover that defines a proximal end and distal end; a motor disposed with the outer cover; a drive shaft coupled to the motor; and a drive coupler disposed at distal end of the handpiece and coupled to the drive shaft, the drive coupler comprising at least one lobe extending radially outward from a distal side of the drive coupler, wherein the at least one lobe comprises a rake that slopes toward the proximal end of the handpiece.

In an alternate embodiment, an instrument for a surgical system, the instrument comprising: an elongate shaft comprising a tip at a distal end; a resection member telescoped with the elongate shaft; a drive coupler coupled to the resection member at a proximal end of the instrument, the drive coupler comprising an at least one lobe extending radially outward from a central axis of the resection member, wherein the at least one lobe comprises a blade shape comprising a leading edge, a trailing edge, a rake, a blade tip between the leading and the trailing edges that defines a length of the blade from the outside surface of the elongate shaft; and wherein the proximal end of the elongate shaft is configured to couple to a second component via the at least one lobe.

BRIEF DESCRIPTION OF THE DRAWINGS

For a detailed description of exemplary embodiments, reference will now be made to the accompanying drawings in which.

DEFINITIONS

Figure 1:
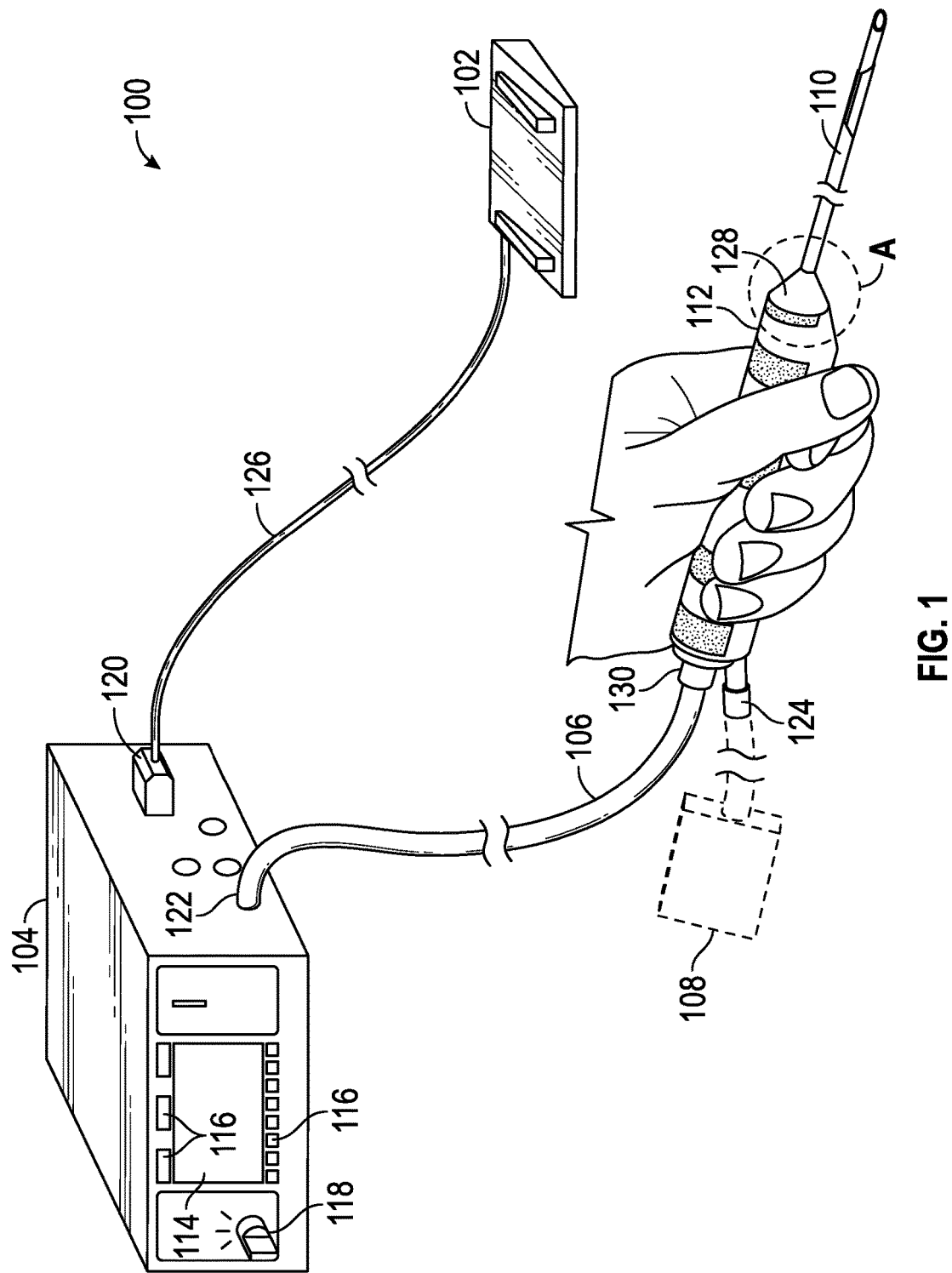
FIG. 1 shows a surgical system that may be used for various surgical procedures including tissue resection and removal according to embodiments of the present disclosure.

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct. Thus, if a first device couples to a second device, that connection may be through a direct connection or an indirect connection via other devices and connections.

"Removably coupled" shall mean a first component coupled to a second component such that first component can be decoupled from the second component without destroying or rendering the first or second components non-functional.

"Lobe" shall mean a shape including a leading edge, a trailing edge, a rake, a tip between the leading and the trailing edges, and a radial distance from the outside surface of the drive coupler to the tip.

"Mating mechanism" shall mean a feature formed on an interior surface of a drive hub and configured to couple to at least one lobe of a drive coupler when the drive hub is partially telescoped over the drive coupler such that the drive coupler and drive hub are secured for operation during a surgical procedure.

"Self-aligning" shall mean that, when force is applied along a shared central axis to telescope a first component over a second component, at least one of the components rotates about the shared central axis in response to an axial force applied along the central to align and engage coupling features of the first and second components to couple the first and the second components.

"Pliable component" shall mean a component fabricated from flexible, semi-flexible, or semi-rigid material including polymers that is used to promote locking/coupling and to account for variation in tolerances between mating parts.

"Slope" in reference to a feature that "slopes toward" a delineated direction shall mean that the feature gets wider toward the delineated direction.

DETAILED DESCRIPTION

The following discussion is directed to various embodiments of the self-aligning drive coupler. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Currently employed surgical devices use a handset coupled to an instrument, and may use a driver such as an electric motor within the handset to drive the instrument. Rotational motion from the electric motor is transferred using an interconnection component. Sometimes, these instruments are engaged with the handset by pushing a first component of the instrument into the interconnection component of the handset. That is, the first component of the handset is inserted into the interconnection component, but, depending on the relative orientation of the devices the first component may not insert itself in the interconnection component and further user interaction may be required to cause rotational engagement of the first component and the interconnection component. Currently employed first components have typically been similar to a two pronged fork with a slot that would accept a mating feature of the interconnection component. The first component can be thought of as the female part of the engagement and the mating feature of the interconnection component can be thought of as the male part of the engagement. Some instruments that resect tissue enable the fluid and tissue to be drained around the coupling components. Using these configurations, remnants of tissue may not be properly cleaned from the device due to inaccessible geometry and features.

In contrast, the handheld surgical device discussed herein may comprise a handset (which may also be referred to as a handpiece), an instrument, a drive coupler attached to a motor shaft of the handset on a first end and inserted into a drive hub coupled to the instrument on a second end. The head of the drive coupler may be elliptical and helical such that, if the drive hub is incorrectly aligned with the drive coupler, the axial force used to telescope the drive coupler into the drive hub will cause rotation of one or both of the drive hub and drive coupler, and the rotation results in proper alignment and orientation of the drive coupler to the drive hub. In one example, the drive coupler may be attached to a motor shaft. In another example, the drive coupler may be designed into the motor shaft. In alternate embodiments, the drive coupler may be coupled to an instrument or designed as an integral part of an instrument shaft, and the drive hub may be attached to the motor shaft or designed as an integral part of the motor shaft.

In an embodiment, the drive coupler has an elliptical base and an elliptical-to-circular frustum for the head. In a first example situation, the drive hub and coupler are perfectly aligned and will couple without relative rotation. If there is any misalignment, the axial force used to insert the drive hub onto the drive coupler will cause relative rotation around the central axis and result in proper alignment and coupling. The drive coupler may comprise stainless steel, aluminum, or a polymer chosen from the group consisting of polyetheretherketone or polyetherimide. The drive hub comprises a polymer such as nylon, acrylonitrile butadiene styrene (ABS) and a polycarbonate (PC). In some embodiments, a pliable component may be coupled to the inner surface of the drive hub and may be employed to account for axial tolerances.

If the frustum of a drive coupler is misaligned with the drive hub, for example, by up to 90 degrees, a drive hub may be telescoped over the drive coupler along a central axis, and at least one of the drive hub and/or the drive coupler will rotate around the central axis in response to the axial force until it the drive coupler mates with the drive hub. In one example, there may be at least one engagement feature on the side (end) of the drive coupler that engages with the drive hub. The engagement feature may be referred to as a lobe and may take on various geometries. In some embodiments, the lobe comprises a propeller blade shape including a blade tip. The engagement feature may be configured to engage with the drive hub by rotating around a central axis in response to the application of axial force when the drive hub is telescoped over the drive coupler. In an embodiment when more than one lobe is present, the two or more lobes may be disposed circumferentially and equidistant around an end of the drive coupler. In alternate embodiments, one or more lobes may be placed at varying distances from each other around an end of the drive coupler. A circular section at the end of the drive coupler enables the drive coupler to begin insertion into the drive hub irrespective of the relative orientation of the drive hub to the drive coupler.

The drive coupler has smooth open surfaces and a male connection that make it easier to clean. The shapes and geometry of the frustum or the base of the drive coupler can be changed from elliptical and circular as well as to other shapes. The length of the base and the frustum can be changed, as can the pitch and other dimensions, in particular the mating dimensions. In various embodiments, the material of the drive coupler can be changed from 304 to other grades of stainless steel (SS) or to aluminum (Al) or other metals as well as plastics such as peek or amorphous thermoplastic polyetherimide (PEI) resins such as ULTEM™. The drive hub can be made from other low friction materials such as nylon, ABS or PC.

FIG. 1 shows a surgical system 100 that may be used for various surgical procedures including tissue resection and removal. In an embodiment, the system 100 comprises a control unit 104 coupled to a handset 112 via a line 106. The handset 112 may comprise a motor drive unit (MDU) as well as a suction and/or fluid line. The control unit 104 may be coupled a proximal end 130 of the handset 112 via the line 106 to supply power to the handset 112, such power may be regulated by the use of a foot switch 102. The control unit 104 may comprise a digital interface 114 that may be a graphical user interface and, in some embodiments, the digital interface 114 may be a touch screen. In some embodiments, a battery may be used to power the handset 112, in which case the control unit 104 and/or foot switch 102 may be omitted. When present, the control unit 104 may be coupled to a wall outlet or may comprise a rechargeable battery and may comprise a plurality of buttons 116 that may aid in the use and control of the operation of the handset 112. The system 100 further comprises a power port 120 of the control unit 104 that may be coupled to a foot switch 102 via a line 126. The handset 112 may be coupled to an instrument 110 at the distal end 128 of the handset 112; the instrument 110 may comprise a burr, blade, or other instrument 110. The handset 112 may also comprise at least one circuit board (not shown) and a plurality of motion, force, and temperature sensors (not shown). In an embodiment, measurements taken by the sensors may be displayed using the digital interface 114.

Figure 2A:
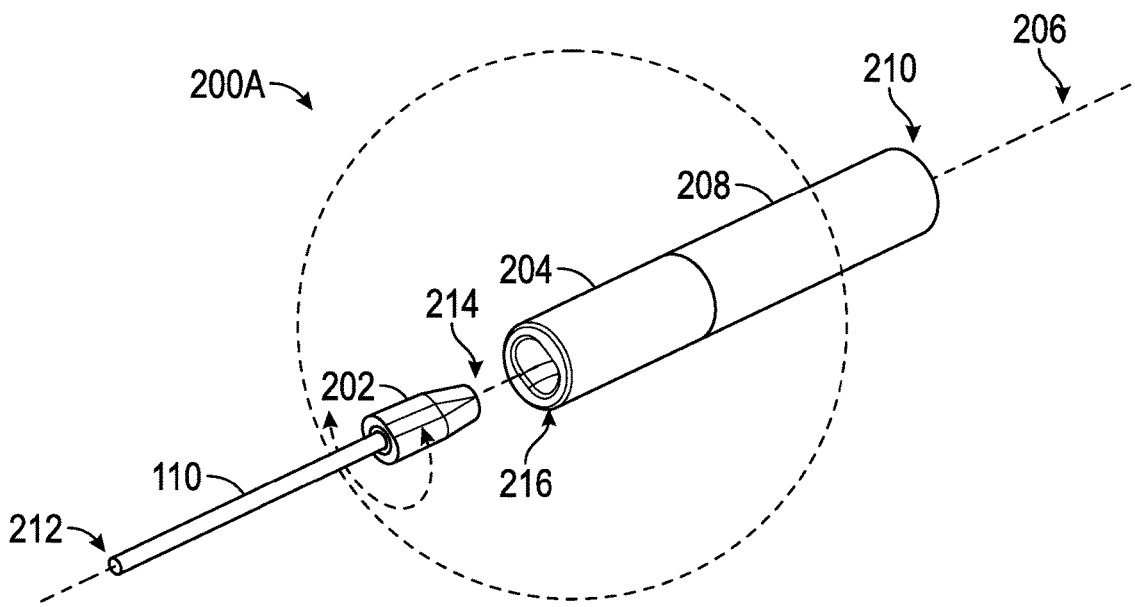
FIGS. 2A-2B show configurations of a surgical device according to embodiments of the present disclosure.
Figure 2B:
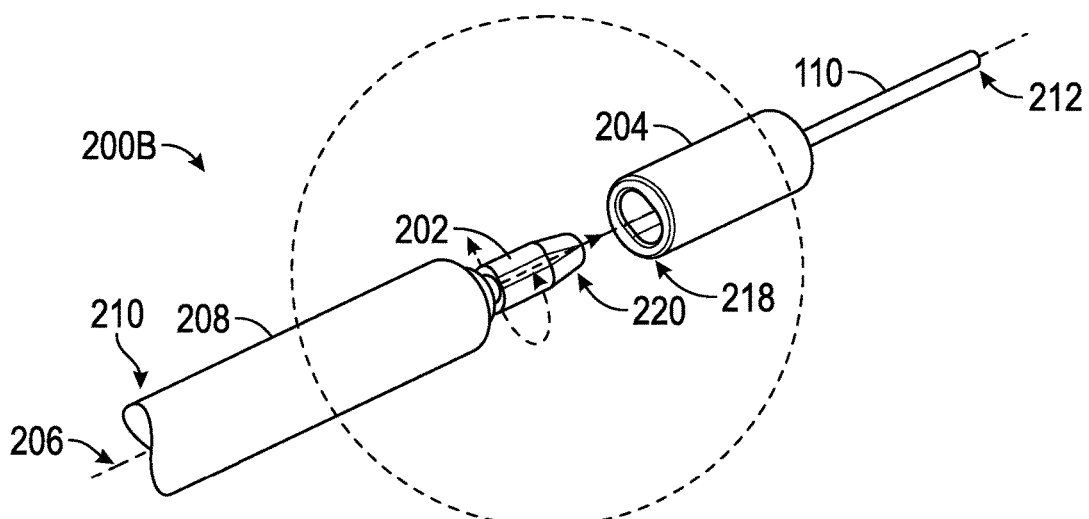

In an embodiment the rotational, axial, and other motion of the instrument 110, may be controlled by a motor within the handset 112 (motor not shown) activated by the foot switch 102. In an embodiment, there may also be a suction source 108 coupled to the handset 112 via a fluid line 124, the fluid line 124 extends from the proximal end 130 of the handset towards the distal end 128, and is shown in more detail below. In an alternate embodiment, the suction source 108 may be omitted and replaced by a fluid source, such that fluid flows into the instrument 110 and out the distal end thereof. Also shown in FIG. 1 is circled a coupling area "A," where the handset 112 is coupled to, e.g., rotationally and axially engaged with, the instrument 110. The coupling area "A" may comprise various configurations as shown in FIGS. 2A and 2B below. Also shown in FIG. 1 is circled a coupling area "A," where the handset 112 is coupled to, e.g., rotationally and axially engaged with, the instrument 110. The coupling area "A" may comprise various configurations as shown in FIGS. 2A and 2B below.

FIGS. 2A and 2B are partial illustrations employed to show embodiments of various assembly configurations with respect to the drive hubs and drive couplers. Thus, both the instruments 110 and the MDU 208 will comprise and/or are coupled to additional components, but such additional components are omitted so as not to obscure the discussion of the possible configurations of the drive hubs and drive couplers.

FIG. 2A illustrates a partial view of a first device configuration 200A according to embodiments of the present disclosure. In the first device configuration 200A, there is a proximal end 210 and a distal end 212, the distal end 212 comprises an instrument 110 and the proximal end 210 comprises an MDU 208. The instrument 110 includes a drive coupler 202 at a proximal end 214 of the instrument 110. The drive coupler 202 comprises at least one lobe and is configured to couple to a drive hub 204, which couples to an MDU 208 at the distal end of the MDU 208.

The proximal end 214 of the instrument 110, e.g., at least a portion of the drive coupler 202, is telescoped into a distal end 216 of the drive hub 204 along the central axis 206. If the at least one lobe of the drive coupler 202 is misaligned with the interior of the drive hub 204 when the drive coupler 202 is telescoped into the drive hub 204, at least one of the drive coupler 202 and/or the drive hub 204 rotates about the central axis 206 in response to axial force. That is, if it is assumed the instrument 110 is easier to rotate than the drive coupler 204 coupled to the MDU 208, the instrument 110, via the drive coupler 202 at its proximal end 214, is self-aligning and rotates about the central axis 206 upon insertion in order to couple (engage) the instrument 110 via drive coupler 202 to the drive hub 204. In other cases, the drive coupler 202 (and instrument 110) may stay stationary while the drive hub 204 and motor shaft of the MDU 208 rotate to enable alignment.

FIG. 2B illustrates a second device configuration 200B according to yet still other embodiments of the present disclosure. In the second device configuration 200B, there is a proximal end 210 and a distal end 212, the distal end 212 comprises an instrument 110 and the proximal end 210 comprises an MDU 208. The instrument 110 includes the drive hub 204 at a proximal end 218 of the instrument 110. A proximal end 218 of the instrument 110 is telescoped over a distal end 220 of an MDU 208. More particularly, the distal end 220 of the MDU 208 includes a drive coupler 202, at least a portion of which is telescoped into the proximal end 218 of the drive hub 204 being part of the instrument in this example.

The drive coupler 202 and/or the drive hub 204 may be configured to rotate around the central axis 206 in response to the axial force applied during telescoping. This rotation may occur, for example, if at least one lobe of the drive coupler 202 is misaligned with the drive hub 204. That is, the drive coupler 202 is self-aligning, and rotates or causes the drive hub to rotate, for example, 45-90 degrees around the central axis 206 upon insertion (application of axial force along the central axis 206) in order to couple the drive coupler 202 to the drive hub 204.

In some embodiments, including those illustrated in FIGS. 2A and 2B, the drive coupler 202, drive hub 204, MDU 208, and instrument 110 are components that are separately assembled as a part of the assembly of the handsets 200A and 200B. In alternate embodiments, the drive coupler 202 may be formed as a part of, removably, or permanently coupled to an instrument 110. In other examples, the drive coupler 202 may be formed as a part of, removably, or permanently coupled to the MDU 208.

Figure 3A:
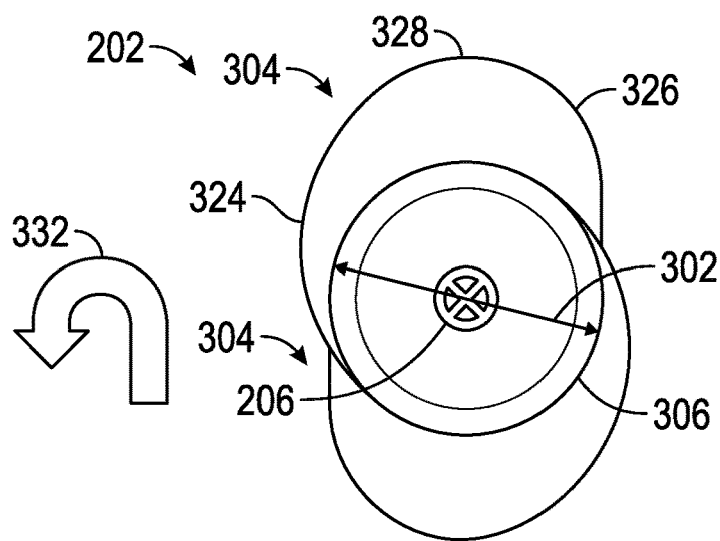
FIGS. 3A, 3B, and 3C show views of a drive coupler according to embodiments of the present disclosure.
Figure 3B:
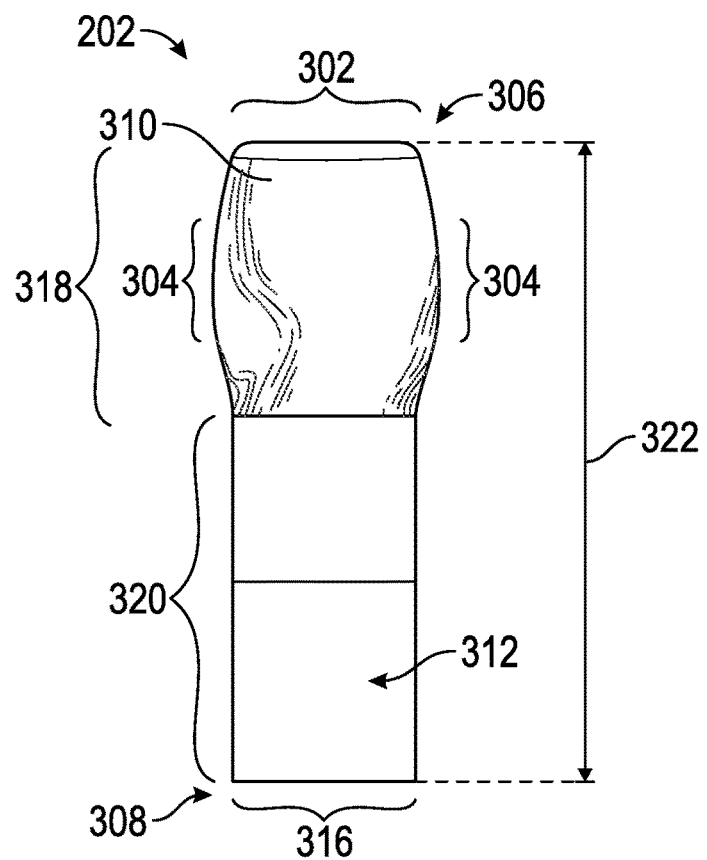
Figure 3C:
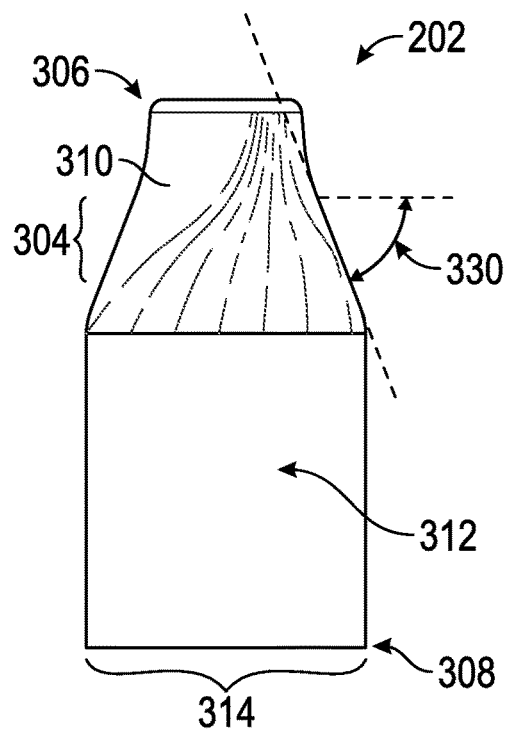

FIGS. 3A, 3B, and 3C illustrate views of the drive coupler 202. FIG. 3A is an overhead view of the drive coupler looking along the central axis 206, and FIGS. 3B and 3C are side views of the drive coupler 202. FIG. 3A illustrates an example drive coupler 202 including two lobes 304, a first end 306, and a diameter 302 of the first end 306. Each lobe 304 may extend radially from the central axis 206 and may comprise a leading edge 324, a trailing edge 326, and a blade tip 328 between the leading 324 and trailing 326 edges. That is, in the configuration shown in FIG. 3A, when the drive coupler 202 is being inserted into a drive hub (not shown in FIG. 3A), and if there is misalignment between the drive coupler 202 and the drive hub, the drive hub 202 rotates in the direction show by arrow 332 until the drive coupler 202 aligns with drive hub. In an embodiment, the pitch direction may be based on the leading edge being axially closer to the first side 306 and the trailing edge 326 being further from the first side 306. As illustrated, the pitch in FIG. 3A results in counter-clockwise rotation (332) for the drive coupler 202 illustrated; however, it is noted that once the drive coupler 202 is coupled to the drive hub, the MDU may turn the drive hub and drive coupler in either direction. The arrow 332 illustrates the possible relative rotation of the drive hub 202 when there is initial misalignment.

FIG. 3B is a first side view of the drive coupler 202. FIG. 3B shows an overall length 322 of the drive coupler, the first side 306 and the second side 308. A first portion 310 may be shaped like a frustum and extends from the first side 306 along a length 318 to abut a second portion 312 that extends from the second side 308 along a length 320. In alternate embodiments, a single lobe 304 or more than two lobes 304 may extend from the first portion 310, and the first portion 310 may take various cross-sectional shapes in order to accommodate features including the lobes 304. In various embodiments, the second portion 312 may comprise an elliptical cross-section defined by a first diameter 316 (FIG. 3B) and a second diameter 314 (as shown in FIG. 3C).

FIG. 3C illustrates a second side view of the drive coupler 202 (rotated 90 degrees from the view of FIG. 3B), including the second diameter 314 of the second portion 312. As shown in FIG. 3C, a rake 330 of the lobes 304 may be towards the second end 308 of the drive coupler 202. When the drive coupler 202 is part of the MDU, the rake of the lobe slopes toward a proximal end of the handpiece. When the drive coupler 202 is part of the instrument, rake of the lobe slopes toward a distal end of the instrument.

Figure 4A:
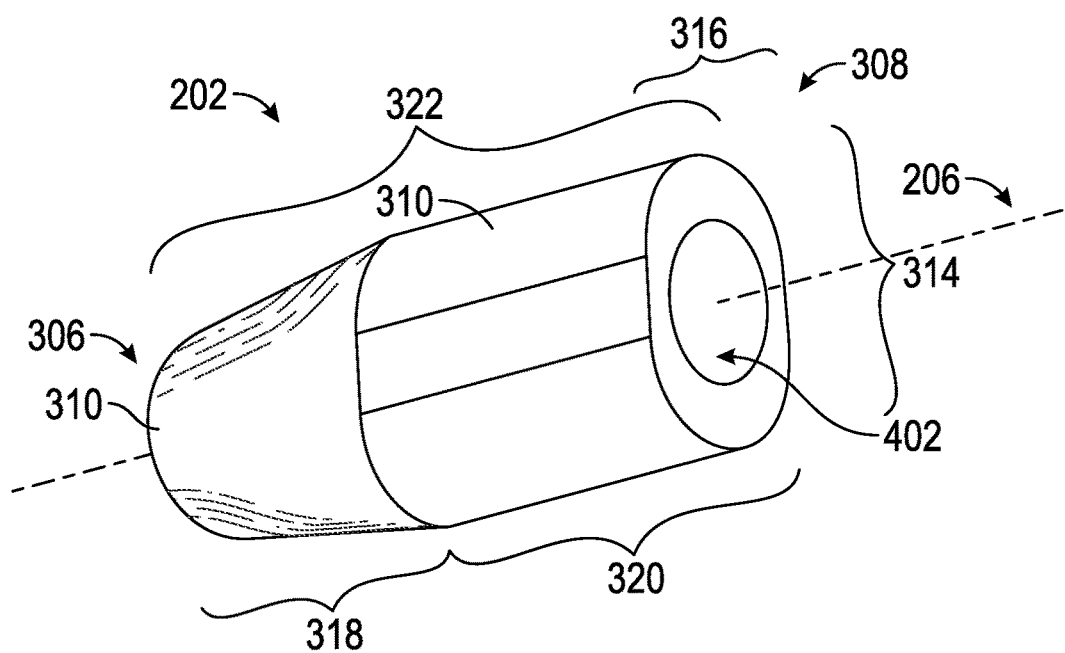
FIG. 4A is a perspective view of the drive coupler according to embodiments of the present disclosure.
Figure 4B:
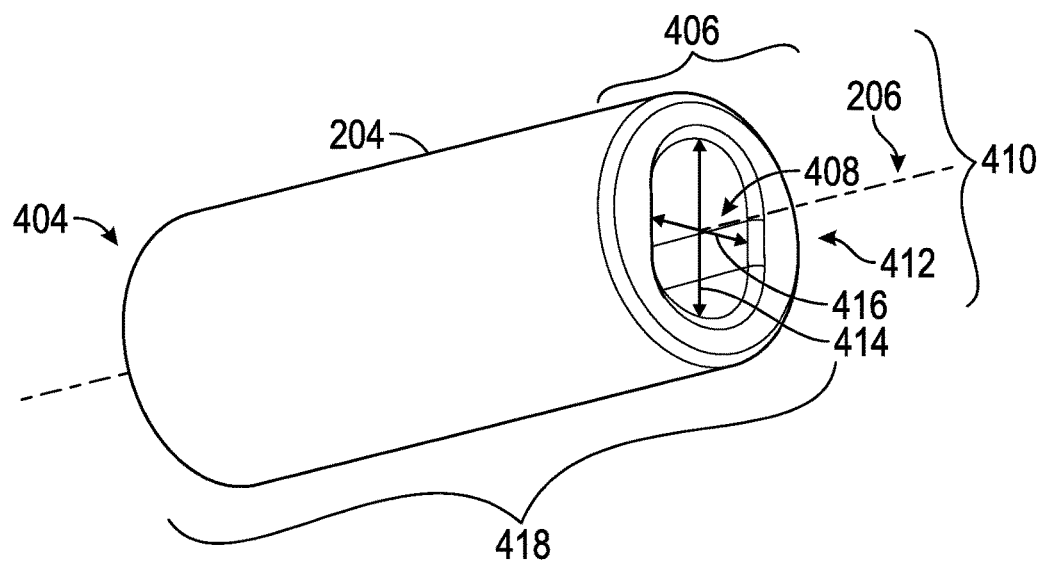
FIG. 4B is a perspective view of the drive hub according to embodiments of the present disclosure.
Figure 4C:
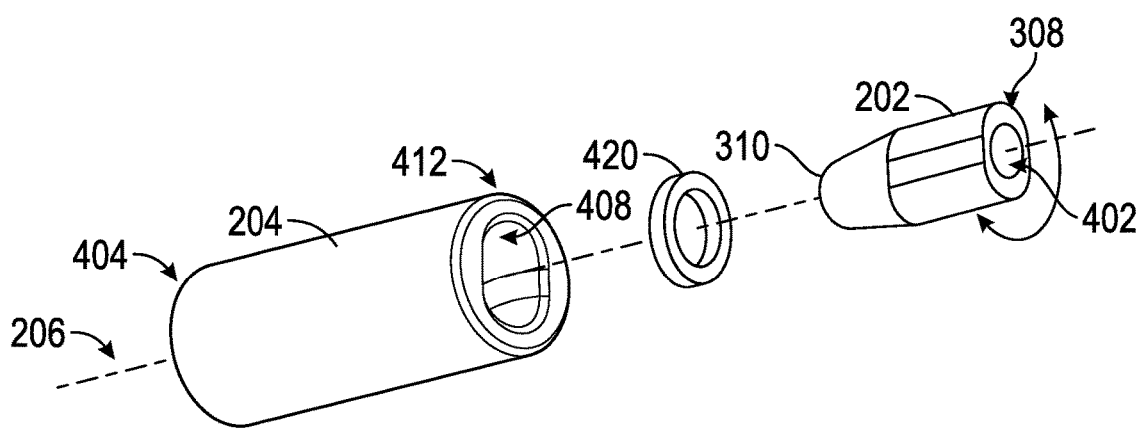
FIG. 4C is an illustration of the drive hub being telescoped over the drive coupler according to embodiments of the present disclosure.

FIGS. 4A and 4B are perspective views of the drive coupler and drive hub, respectively, and FIG. 4C shows an assembly of the drive hub and the drive coupler. FIG. 4A shows the channel 402 of the drive coupler 202, the first diameter 316, and the second diameter 314 of the second portion 320. The channel 402 may comprise a maximum diameter and a minimum diameter and may comprise a cross-sectional shape of a circle, oval, or ellipse, but in most cases the channel 402 defines a circular cross-section to fit over the motor shaft (if the drive coupler is part of the handset), or to fit over the rotating portion of the instrument (if the drive coupler is part of instrument). In some examples, a set screw (not specifically shown) may be employed to couple the drive coupler 202 to the MDU or to the resection device by way of the channel 402.

FIG. 4B is a perspective view of the drive hub 204. FIG. 4B illustrates the drive hub 204, including a first side 404, a second side 412, and a channel 408 configured to mate with the first portion 310 of the drive coupler 202 as shown in FIG. 4A. The drive hub 204 comprises an overall length 418, a first inner diameter 414 and a second inner diameter 416 that define in part the channel 408. The drive hub 204 further comprises a first outer diameter 410 and a second outer diameter 406, which may be equal or different to form a circular, oval, or elliptical cross section. The channel 408 defines an interior surface, and the interior surface defines a cross-sectional shape that matches the cross-sectional shape second portion 320 (FIG. 4A) of the drive coupler 202. In alternate embodiments, a set screw (not shown) may be disposed to couple the drive hub 204 to an instrument.

FIG. 4C is an exploded perspective view of components of the assembly of the drive coupler 202 and the drive hub 204. In FIG. 4C, the first side 310 of the drive coupler 202 is aligned with the second end 412 of the drive hub 204 along the central axis 206. If the drive coupler 202 is misaligned with the drive hub 204, in particular the channel 408 of the drive hub 204, the drive coupler 202 (or the drive hub) may rotate around the central axis 206 until the lobe or lobes align with a mating mechanism on the interior of the drive hub 204 in the channel 408. As the drive coupler 202 and drive hub 204 align rotationally, the drive coupler telescopes at least partially within the drive hub such that the first lobe 304 engages with a portion of the cross-sectional shape of the channel 408. In some embodiments, a pliable feature 420 may be disposed in the channel 408 of the drive hub 204 in order to account for tolerances between the drive coupler lobes 304 and the inner surface of the channel. This pliable feature 420 may comprise an O-ring or another shape as appropriate for the device configuration. The pliable feature 420 may be employed to account for axial tolerances, e.g., to push the drive hub 204 towards the distal end of the device.

Figure 5A:
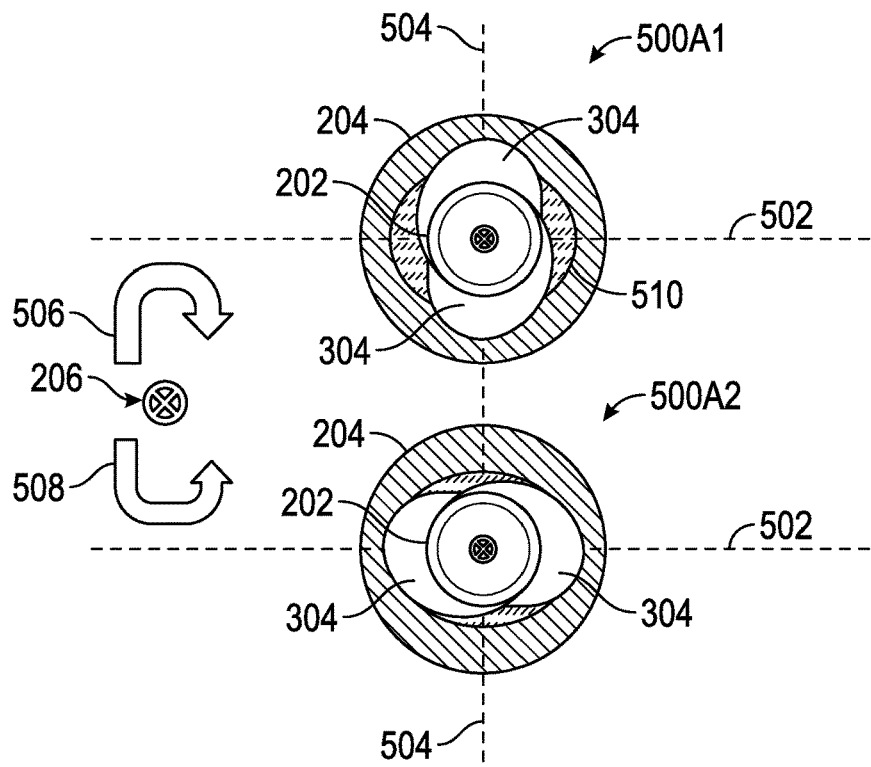
FIGS. 5A and 5B show the self-alignment of the drive hub with the drive coupler when the drive coupler is misaligned with and telescoped through the drive hub according to embodiments of the present disclosure.
Figure 5B:
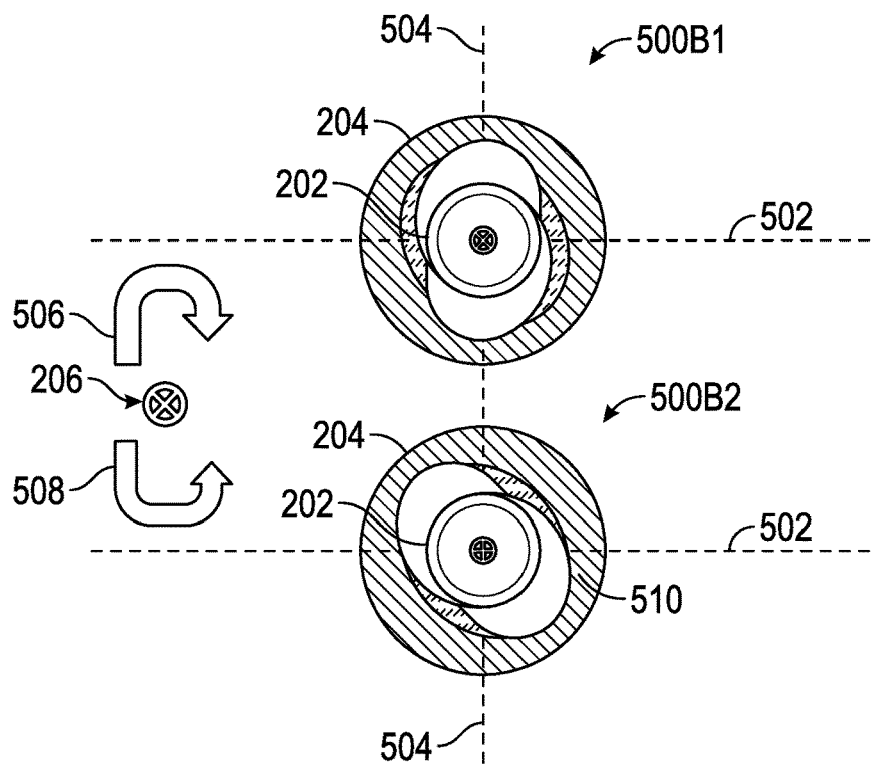

FIGS. 5A and 5B show the self-alignment of the drive hub 204 with the drive coupler 202 when the drive coupler 202 is partially telescoped into the drive hub 204 and is not aligned (is misaligned) with the drive hub 204. In FIG. 5A, the lobes 304 are aligned in 500A1 with an axis 504 which is perpendicular to the central axis 206. When axial force is applied along the central axis, e.g., into the page, the drive coupler 202 may rotate in a first direction 506 or in a second direction 508 depending upon the pitch of the rake portion. As shown in 500A2, the drive coupler 202 may rotate approximately 90 degrees in the direction 506 so that the lobes 304 engage with an inner surface 510 of the drive hub 204. The term "inner surface" 510 is used herein to describe the interior of the channel 408 shown in FIG. 4B.

In FIG. 5B, the self-alignment of the drive hub 204 and drive coupler 202 is further illustrated. In 500B1 of FIG. 5B, the lobes 304 are aligned with an axis 504 which is perpendicular to the central axis 206. When axial force is applied along the central axis 206, e.g., into the page, the drive coupler 202 may rotate in direction a first direction 506 or in a second direction 508 around the central axis 206 depending on the angle of the pitch. As shown in 500B2 approximately 45 degrees in the 508 direction so that the lobes 304 engage with an inner surface 510 of the drive hub 204. It is understood that the alignment of the lobes 304 with the axis 504 in FIGS. 5A and 5B is merely illustrative for purposes of description, and that the self-alignment of the drive hub 204 and the drive coupler 202 occurs when axial force is applied along 206 when there is any misalignment between the drive hub 204 and the drive coupler 202 such that would cause rotation of the drive hub 204 or the drive coupler 202 in order for the lobes 304 to engage the inner surface 510. That is, the alignment between the drive coupler 202 and the drive hub 204 occurs when the drive hub 204 is telescoped over the drive coupler 202 without additional manual intervention (e.g., no manual rotation about the central axis 206) because the device is self-aligning.

Figure 6:
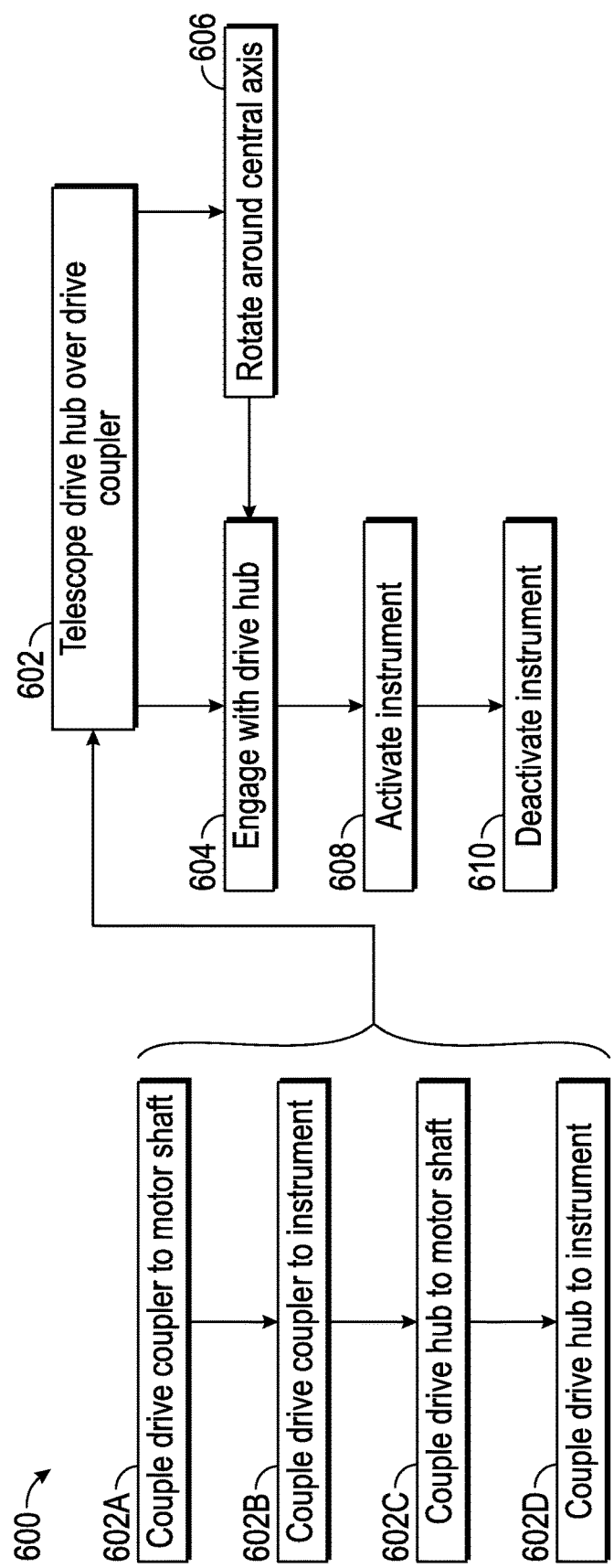
FIG. 6 is a flow chart of a method of assembling a surgical device according to embodiments of the present disclosure.

FIG. 6 is a flow chart of a method 600 of assembling a surgical device. The method 600 comprises, at block 602, telescoping a drive hub over a portion of a drive coupler along a central axis, the drive coupler comprising a first lobe extending radially outward. In some embodiments, the drive coupler may comprise a plurality of lobes extending radially outward which may be arranged equidistant from each other or at other distances around the drive coupler. In an embodiment at block 604, the telescoping at block 602 causes the first lobe to engage with a mating mechanism of the drive hub. In an alternate embodiment at block 606, the telescoping at block 602 causes the relative axial rotation as between the drive hub and the drive coupler until the first lobe of the drive coupler is aligned with and engages with a mating mechanism of the drive hub at block 604. In an alternate embodiment where there are two or more lobes extending radially from the drive coupler, causing relative axial rotation at block 606 further comprises causing relative axial rotation between the drive hub and the driver coupler until the first lobe and second lobe are aligned with and engage with the mating mechanism at block 604. While the telescoping at block 602 along a central axis is described as a separate block from the rotation around the central axis at block 606, it is appreciated that the rotation at block 606 is in response to and occurs during the telescoping at block 602 if there is a misalignment between the drive hub and drive coupler.

In an embodiment, the telescoping at block 602 further comprising telescoping the drive hub over the portion of the drive coupler when the first one lobe and the mating mechanism are misaligned by about 90 rotational degrees, and the rotation at block 606 may be about 90 degrees.

In an alternate embodiment, the telescoping at block 602 further comprising telescoping the drive hub over the portion of the drive coupler when the first one lobe and the mating mechanism are misaligned by from about 45 rotational degrees to about 90 rotational degrees and the rotation at block 606 may be from about 45 degrees to about 90 degrees.

In various embodiments, prior to telescoping the drive hub over the drive coupler at block 602, the drive coupler may be coupled to the motor shaft at block 602A, and/or the drive coupler may be coupled to the instrument at block 602B. In another embodiment, prior to telescoping the drive hub over the drive coupler at block 602, at block 602C, the drive hub is telescoped over a portion of the drive coupler at a first side of the drive coupler, and, at block 602D, the drive hub may be coupled to the instrument. At block 608, power may be supplied to the handpiece and the instrument is activated, in particular, the motor is activated in response to the power and wherein the instrument is in motion while power is supplied to the handpiece. The handpiece may be deactivated at block 610 when the surgical procedure or a portion of the surgical procedure is completed.

The above discussion is meant to be illustrative of the principles and various embodiments of the present invention. Numerous variations and modifications will become apparent to those skilled in the art once the above disclosure is fully appreciated.

The invention claimed is:

1. A surgical system comprising:
   a handpiece comprising a proximal end, a distal end, and a motor that defines a drive shaft;
   a drive hub comprising an interior surface, and an exterior surface, the interior surface defines a cross-sectional shape, and the drive hub coupled to the drive shaft;
   a drive coupler having an exterior surface defining a continuously curved configuration about a periphery thereof, the drive coupler comprising a first lobe defining a first portion of the exterior surface and extending radially from a central axis of the drive coupler, the first lobe positioned off-center relative to the central axis such that the first portion of the exterior surface extends eccentrically relative to the central axis, the drive coupler telescoped at least partially within the drive hub such that the first portion of the exterior surface engages a portion of the interior surface of the drive hub; and
   an instrument comprising an elongate shaft and resection member telescoped within the elongate shaft, the resection member coupled to the drive hub.

2. The system of claim 1, further comprising:
   wherein the drive coupler is coupled to the drive shaft such that a rake of the first lobe slopes toward a proximal end of the handpiece; and
   wherein the drive hub is coupled to the resection member such that an aperture leading to the interior surface is on a proximal end of the drive hub.

3. The system of claim 1, further comprising:
   wherein the drive coupler is coupled to a proximal end of the resection member such that a rake of the first lobe slopes toward a distal end of the instrument; and
   wherein the drive hub is coupled to drive shaft such that an aperture leading to the interior surface is on a distal end of the drive hub.

4. The system of claim 1, wherein the drive coupler comprises stainless steel, aluminum, or a polymer selected from the group consisting of: polyetheretherketone or polyetherimide.

5. The system of claim 1, wherein the drive hub comprises a polymer selected from the group consisting of: nylon, ABS, or PC.

6. The system of claim 1, further comprising a controller coupled to a power source and to the motor.

7. The system of claim 1, further comprising a second lobe defining a second portion of the exterior surface and extending radially from the central axis of the drive coupler opposite the first lobe, wherein the second lobe comprises a shape comprising a leading edge, a trailing edge, a rake, a blade tip between the leading and the trailing edges.

8. The system of claim 7, wherein the first lobe and the second lobe define a cross-sectional area that corresponds to the cross-sectional shape of the interior surface of the drive hub.

9. The system of claim 1, further comprising a pliable component disposed on the interior surface of the drive hub.

10. The system of claim 9 wherein the pliable component is in contact with an outside surface of the drive coupler when the drive hub is telescoped over the portion of the drive coupler.

11. The system of claim 1, wherein the handpiece further comprises a battery.

12. A method of assembling a surgical device, comprising:
    initially telescoping a drive hub over a portion of a drive coupler along a central axis, the drive coupler having an exterior surface defining a continuously curved configuration about a periphery thereof, the drive coupler comprising a first lobe defining a first portion of the exterior surface and extending radially outward from the central axis, the first lobe positioned off-center relative to the central axis such that the first portion of the exterior surface extends eccentrically relative to the central axis, wherein, during the initial telescoping, the first portion of the exterior surface contacts a portion of an interior surface of the drive hub; and
    further telescoping the drive hub over a further portion of the drive coupler along the central axis, thereby causing relative axial rotation between the drive hub and the drive coupler and relative sliding between the first portion of the exterior surface and the portion of the interior surface until the first lobe of the drive coupler is aligned with and engages with a mating mechanism of the drive hub.

13. The method of claim 12, wherein telescoping further comprises:
    even further telescoping the drive hub over an even further portion of the drive coupler and coupling the drive coupler to a handpiece, wherein the drive coupler is coupled to a drive shaft of a motor of the handpiece.

14. The method of claim 12, further comprising supplying power to the handpiece, wherein the motor is activated in response to the power and wherein the instrument is in motion while power is supplied to the handpiece.

15. The method of claim 12,
    wherein the drive coupler further comprises a second lobe extending radially outward opposite the first lobe to define a second portion of the exterior surface that extends eccentrically relative to the central axis; and
    wherein causing relative axial rotation further comprises causing relative axial rotation between the drive hub and the driver coupler until the first lobe and second lobe are aligned with and engage with the mating mechanism.

16. The method of claim 12, wherein, during the initial telescoping, the first lobe and the mating mechanism are misaligned by about 90 degrees.

17. The method of claim 12, wherein, during the initial telescoping, the first lobe and the mating mechanism are misaligned by from about 45 degrees to about 90 degrees.

18. A handpiece for a surgical system, the handpiece comprising:
    an outer cover that defines a proximal end and distal end;
    a motor disposed with the outer cover;
    a drive shaft coupled to the motor; and
    a drive coupler having an exterior surface defining a continuously curved configuration about a periphery thereof, the drive coupler disposed at distal end of the handpiece and coupled to the drive shaft, the drive coupler defining a central axis and comprising at least one lobe extending radially outward from the drive coupler to define at least a first portion of the exterior surface that extends eccentrically relative to the central axis, wherein the at least one lobe comprises a rake that slopes toward the proximal end of the handpiece.

19. The system of claim 18, wherein the distal side of the drive coupler comprises a conical frustum tapered towards the distal end of the handpiece.

20. The system of claim 18, wherein the at least one lobe comprises a propeller blade shape defined by a blade tip.

21. The system of claim 18, further comprising a second lobe extending radially outward from the drive coupler 180 degrees from the first lobe, the second lobe defining a second portion of the exterior surface that extends eccentrically relative to the central axis.

22. The system of claim 21, wherein a rake of the second lobe slopes toward the proximal end of the handpiece.

23. The system of claim 22, wherein the rake of the at least one lobe is substantially similar to the rake of the second lobe.

24. An instrument for a surgical system, the instrument comprising:
   an elongate shaft comprising a tip at a distal end;
   a resection member telescoped with the elongate shaft;
   a drive coupler having an exterior surface defining a continuously curved configuration about a periphery thereof, the drive coupler coupled to the resection member at a proximal end of the instrument, the drive coupler comprising at least one lobe extending radially outward from a central axis of the resection member to define a first portion of the exterior surface that extends eccentrically relative to the central axis of the resection member, wherein the at least one lobe comprises a blade shape comprising a leading edge, a trailing edge, a rake, and a blade tip between the leading and the trailing edges that defines a length of the blade from the outside surface of the elongate shaft; and
   wherein the proximal end of the elongate shaft is configured to couple to a second component via the at least one lobe.

25. The system of claim 24, wherein the drive coupler comprises a plurality of lobes disposed radially about the central axis.

26. The system of claim 24, wherein a cross-sectional shape of the proximal end of drive coupler is elliptical.

* * * * *